United States Patent [19]

Fox et al.

[11] Patent Number: 4,724,550

[45] Date of Patent: Feb. 16, 1988

[54] CAP AND GOGGLE

[76] Inventors: Nelson C. Fox; Rosetta V. G. Fox, both of Ferry Reach, St. George's, Bermuda

[21] Appl. No.: 711,281

[22] Filed: Jul. 9, 1986

[51] Int. Cl.$^4$ .......................... A61F 9/02; A42B 1/12
[52] U.S. Cl. .......................................... 2/428; 2/68; 2/424
[58] Field of Search .................. 2/68, 174, 426, 9, 10, 2/428, 429, 430, 199, 441, 427, 173; 128/201.22

[56] References Cited

U.S. PATENT DOCUMENTS

| 1,200,528 | 10/1916 | Ryder | 2/173 X |
| 1,349,206 | 8/1920 | Jeffers | 2/68 |
| 2,162,608 | 6/1939 | Davis | 2/174 |
| 2,279,435 | 4/1942 | Berg | 2/174 |
| 2,642,574 | 6/1953 | Eloranta | 2/427 X |
| 2,705,802 | 4/1955 | Tellier | 2/68 |
| 2,706,815 | 4/1955 | Parmelee | 2/441 |
| 3,296,582 | 1/1967 | Ide | 2/68 X |
| 3,710,393 | 1/1973 | Douglas | 2/68 X |
| 4,279,039 | 7/1981 | Drew | 2/68 X |

FOREIGN PATENT DOCUMENTS 0657057  8/1986  Switzerland ........................ 2/424

Primary Examiner—Peter Nerbun
Attorney, Agent, or Firm—Berman, Aisenberg & Platt

[57] ABSTRACT

A cap and goggles combination comprises a rubber cap and a face glass which covers the eyes and extends across an upper portion of the nose and cheeks. A rubber frame surrounds the circumference of the face glass, and includes a groove for securely retaining the face glass. The rubber cap covers the user's head, except for the ears and, and is connected to the rubber frame adjacent the top and side edges of the face glass.

2 Claims, 6 Drawing Figures

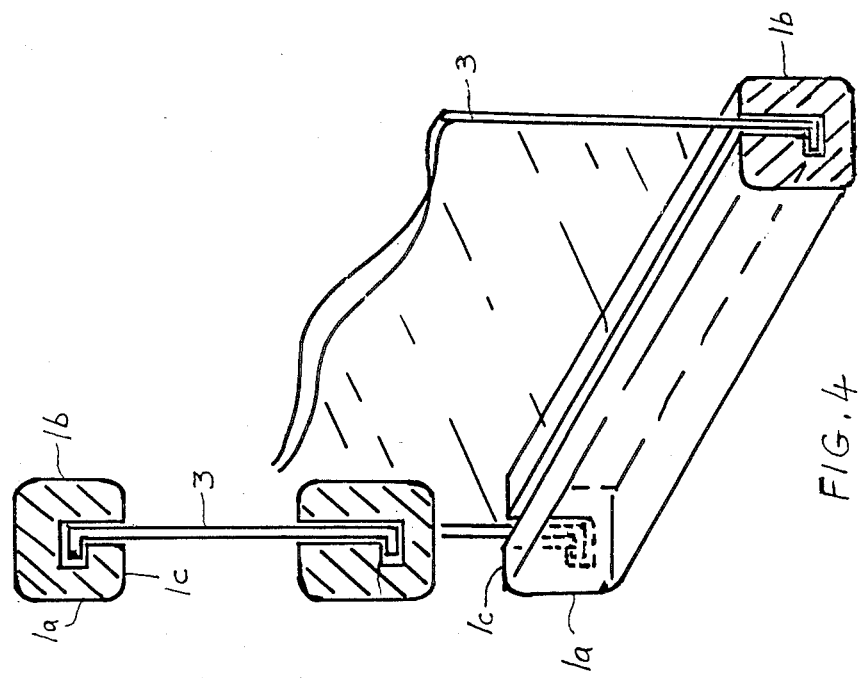
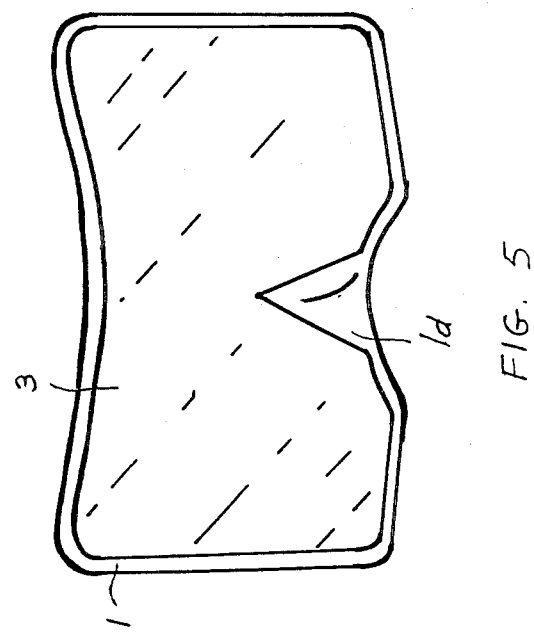

CAP AND GOGGLE

BRIEF SUMMARY OF INVENTION

The cap and goggles combination is a rubber cap that covers the hair and is glued to a rubber frame surrounding a face glass. The glass is inserted in a rubber groove to secure it. The rubber frame that the glass is inserted into is a continuation of the adjoining rubber cap making it an all in one unit. Sizes are made to fit accordingly. The cap has a rubber frame with a groove at the top-front, sides and bottom where the face glass is inserted.

The cap and goggles combination is used as a sea bathing aid for men, women and children when swimming to keep the hair from getting wet, while at the same time protecting the eyes from wet hair and from water entering the eyes.

The combined cap and goggles may be an aid for swimmers in carrying out short expeditions under water.

BRIEF DESCRIPTION OF THE DRAWINGS

FIG. 4 shows two details of insertion of the face glass in the rubber frame: a cross-sectional view and a perspective view.

FIG. 5 is a front elevational view of the face glass.

DETAILED DESCRIPTION

In FIGS. 1 to 6, like numerals represent like parts. The cap and goggles combinations of this invention is referred to generally in FIG. 1. Rubber frame 1 surrounds the outside edge of face glass 3 and is connected to attached rubber cap 5 along portions adjacent the top edge and side edges of the face glass.

Figure 2:
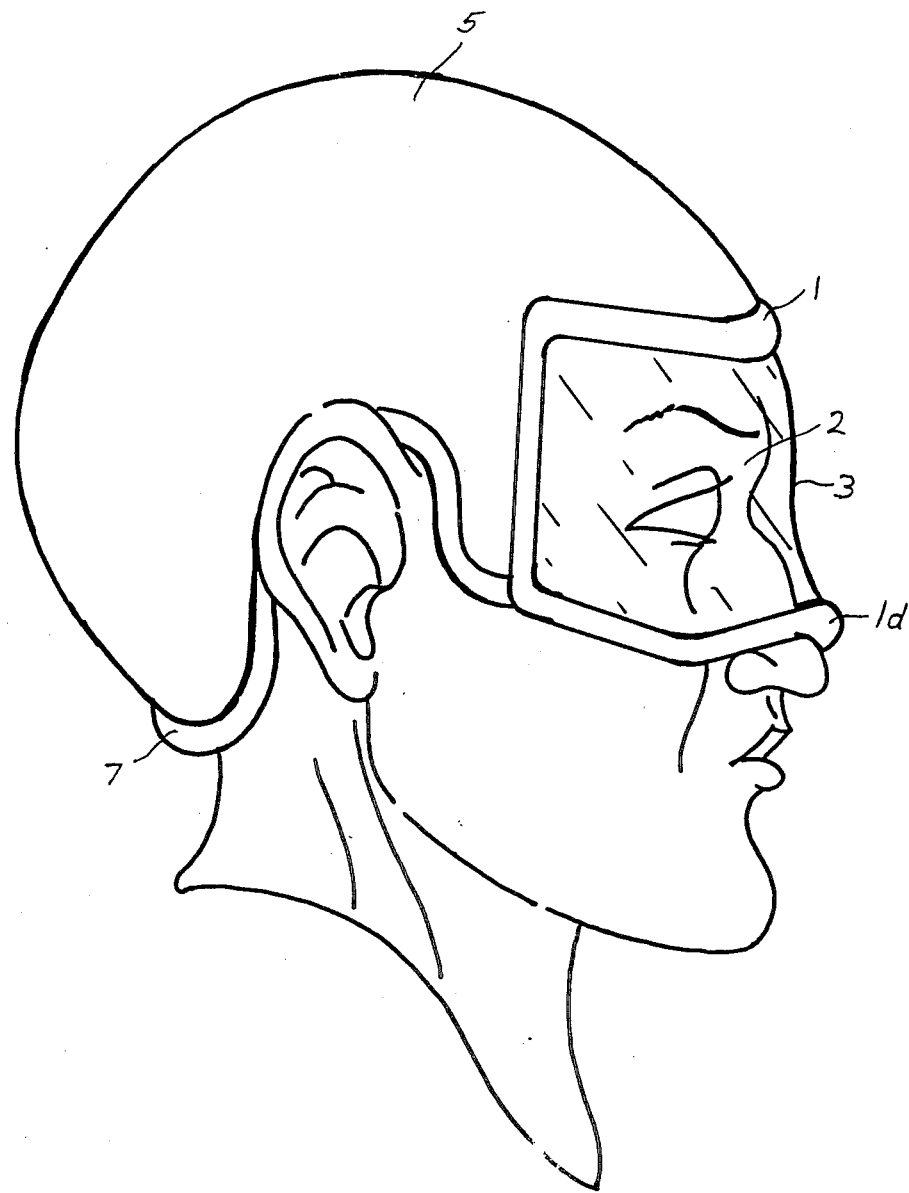
FIG. 2 is a side elevational view of the combination of FIG. 1.

In FIG. 2, face 2 is seen through face glass 3, which may be small, medium, and large, that in turn is inserted in a rubber groove (see FIG. 4) formed in rubber frame 1 that in turn adjoins cap 5.

The face glass 3 shown in FIG. 4 is inserted in outside rubber portion 1b forming a wall of the groove and inside rubber portions 1a, 1c forming additional walls of the groove. Face glass 3, in the lower part of FIG. 4, is shown from an inside view. Rubber portion 1d, FIGS. 1, 2 of the rubber frame above the nose has a thickness shown in FIGS. 1, 2, and 5, so that when the wearer puts the cap and goggles combination on, the rubber stretches to fit tightly preventing water from passing through thus keeping the eye area dry.

Figure 3:
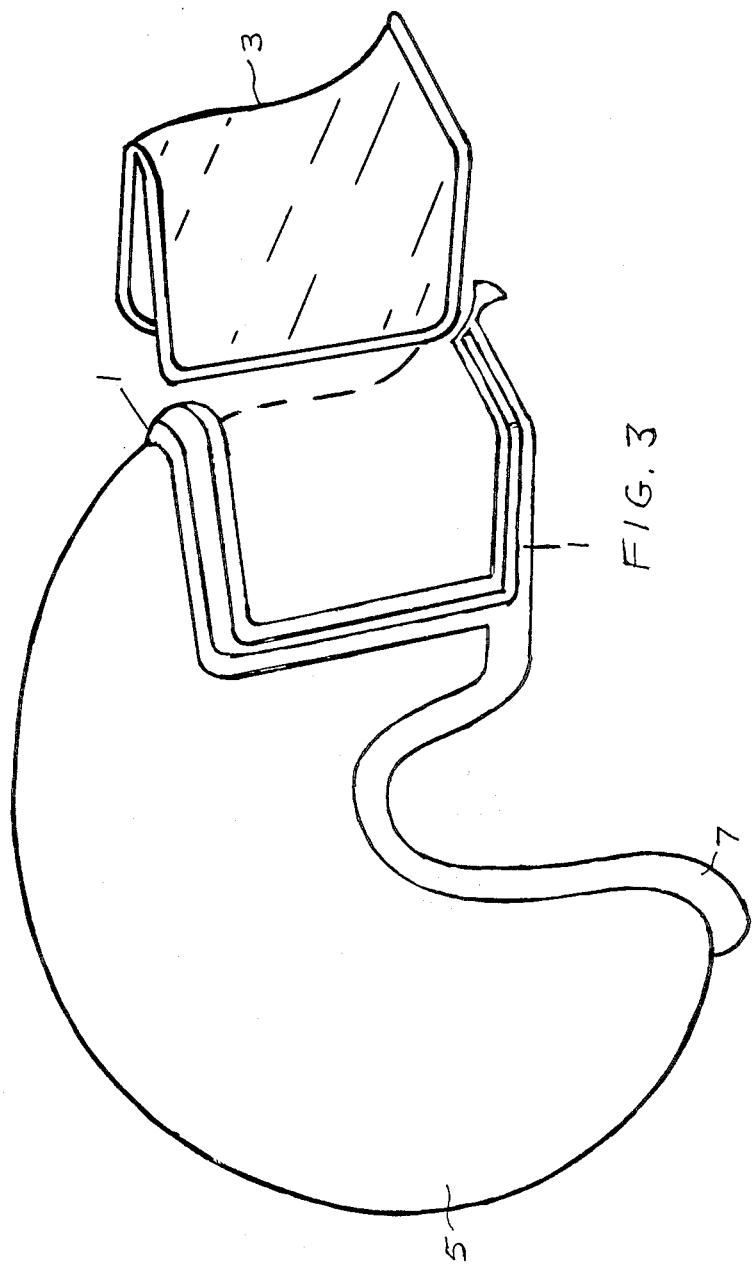
FIG. 3 is a perspective view showing an exploded view of insertion of the face glass into the rubber frame.
Figure 6:
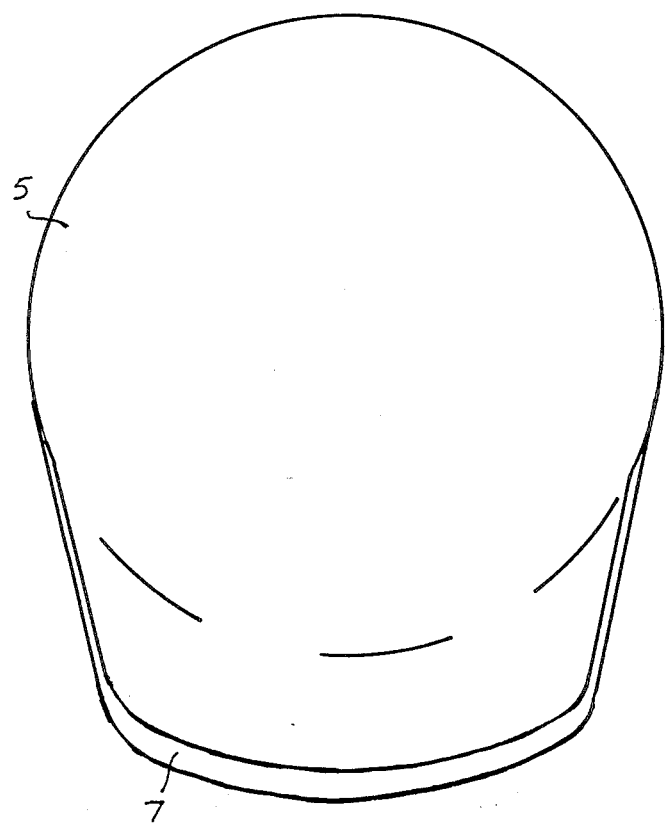
FIG. 6 is a back elevational view of the rubber cap.

Reinforced rubber edge 7 forms a band that has a thickness to prevent water from seeping through when the cap is stretched around the head shown in FIGS. 2, 3, and 6. Rubber cap 5 may be made small, medium or large. The thickness of edge 7 at the circumference around the back of the head, ears, and part of the face is shown in FIGS. 2, 3, and 6.

Figure 1:
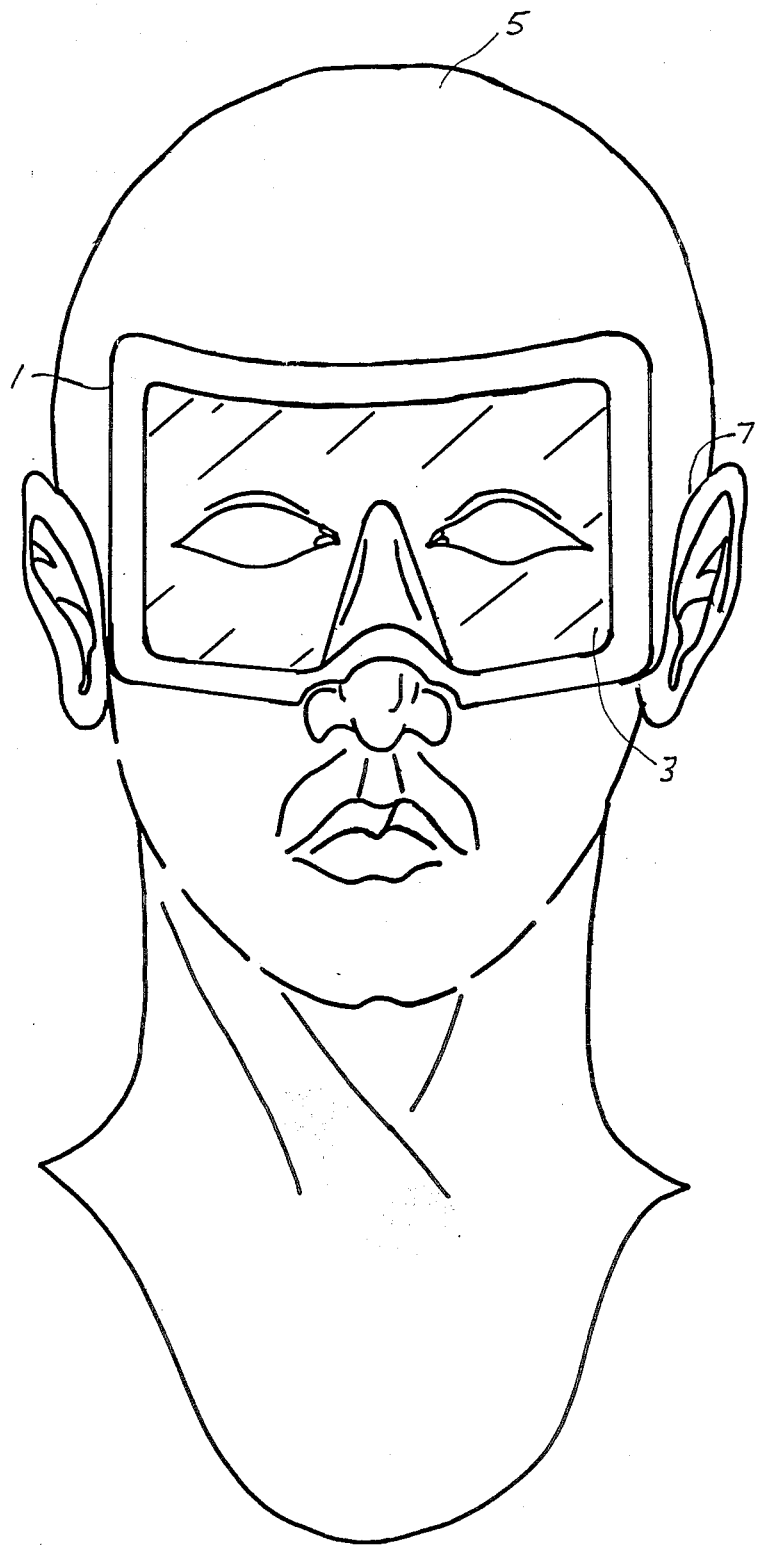
FIG. 1 is a front elevational view of a cap and goggles combination of the invention.

As shown in FIGS. 1 and 2, the face glass 3 extends across an upper portion of the user's nose and cheeks and has a top edge extending substantially horizontally above the user's eyebrows. Further, as seen in FIGS. 1 and 2, face glass 3 has a bottom edge extending substantially horizontally across the user's nose and cheeks and has side edges extending substantially at sides of the user's face. Finally as seen in FIG. 1, the rubber cap 5 covers top, side, and back portions of the user's head with the user's ears remaining uncovered.

We claim:

1. Combined cap and goggles for use in water comprising face glass means, for viewing through by a user, covering a user's eyes and extending across an upper portion of the user's nose and cheeks, having a top edge extending substantially horizontally, above the user's eyebrows, and a bottom edge extending substantially horizontally across the user's nose and cheeks, said top and bottom edges joined by side edges extending substantially at sides of the user's face, rubber frame means surrounding the circumference of said face glass means for securely retaining said face glass means watertightly across the user's nose and cheeks, and rubber cap means for covering the user's head connected to said rubber frame means along portions adjacent said top edge and said edges of said face glass means, said rubber cap means covering top, side and back portions of said user's head, said user's ears remaining uncovered, wherein said frame means includes groove means for securing edges of said face glass means, and said combined cap and goggles is retained securely on the user's head without using securing straps.

2. A combination of claim 1 further comprising band means around the lower perimeter of said cap for excluding water from within the cap.

* * * * *